US007455984B2

(12) United States Patent
Harrison et al.

(10) Patent No.: US 7,455,984 B2
(45) Date of Patent: Nov. 25, 2008

(54) IMMUNOREACTIVE AND IMMUNOTHERAPEUTIC MOLECULES

(75) Inventors: Leonard Harrison, St. Kilda (AU); Margo Honeyman, St. Kilda (AU); George Rudy, Glen Iris (AU); Andrew Lew, Essendon (AU)

(73) Assignee: The Walter and Eliza Hall Institute of Medical Research (AU)

( * ) Notice: Subject to any disclaimer, the term of this patent is extended or adjusted under 35 U.S.C. 154(b) by 172 days.

(21) Appl. No.: 10/040,815

(22) Filed: Jan. 7, 2002

(65) Prior Publication Data

US 2002/0142004 A1 Oct. 3, 2002

Related U.S. Application Data

(62) Division of application No. 08/663,272, filed on Nov. 25, 1996, now Pat. No. 6,818,217.

(30) Foreign Application Priority Data

Feb. 20, 1995 (AU) .................................... PN1239
Sep. 4, 1995 (AU) .................................... PN5172
Feb. 20, 1996 (WO) .................... PCT/AU96/00085

(51) Int. Cl.
  *G01N 33/00* (2006.01)
(52) U.S. Cl. ................................... 435/7.24
(58) Field of Classification Search ................. 435/183, 435/7.1, 7.21; 514/866
  See application file for complete search history.

(56) References Cited

U.S. PATENT DOCUMENTS 5,674,978 A * 10/1997 Tobin et al. ................. 530/326

6,509,165 B1 * 1/2003 Griffin et al. ............... 435/7.24

FOREIGN PATENT DOCUMENTS

| CA | 2194548 | 1/1996 |
| EP | 0171886 A | 2/1986 |
| EP | 0554466 A | 6/1993 |
| WO | WO 92/05446 | 4/1992 |
| WO | WO 92/14485 | 9/1992 |
| WO | WO 92/20811 | 11/1992 |
| WO | WO 94/12529 | 6/1994 |
| WO | WO 95/07464 | 3/1995 |
| WO | WO 95/07992 | 3/1995 |

OTHER PUBLICATIONS

Miyazaki, I., et al. J. Immunol. Feb. 1, 1995; 154:1461-1469.*
Mauch, et al., (1992), "Characterization of a linear epitope within the human pancreatic 64-kDa glutamic acid decarboxylase and its autoimmune recognition by sera from insulin-dependent diabetes mellitus patients", Eur J.Biochem, vol. 212:597-603.
Daw et al., (1995), "Two Distinct Glutamic Acid Decarboxylase Auto-Antibody Specificities in IDDM Target Different Epitopes" *Diabetes*, vol. 44, pp. 216-220.
Rudy, G. et al., "Similar Peptides from Two β Cell Autoantigens, Proinsulin and Glutamic Acid Decarboxylase, Stimulate T Cells of Individuals at Risk for Insulin-Dependent Diabetes", *Molecular Medicine*, 1(6): 625-633 (1995), XP000607204.

* cited by examiner

*Primary Examiner*—G. R Ewoldt
(74) *Attorney, Agent, or Firm*—Scully, Scott, Murphy & Presser, P.C.

(57) ABSTRACT

The present invention relates generally to molecules such as peptides, polypeptides and proteins which interact immunologically with antibodies or T-cells in subjects having pre-clinical or clinical Insulin-Dependent Diabetes Mellitus (IDDM). These molecules are preferentially immunoreactive to T-cells in subjects having pre-clinical or clinical IDDM and are useful in the development of diagnostic, therapeutic and prophylactic agents for IDDM.

3 Claims, 4 Drawing Sheets

IMMUNOREACTIVE AND IMMUNOTHERAPEUTIC MOLECULES

CROSS REFERENCE TO RELATED APPLICATIONS

The present application is a divisional application of U.S. Ser. No. 08/663,272 now U.S. Pat. No. 6,818,217 filed on Nov. 25, 1996, which is a §371 application based on International Patent Application No. PCT/AU96/00085 filed on Feb. 20, 1996, which in turn claims priority from Australian Patent Application No. PN 5172/95 filed on Sep. 4, 1995 and Australian Patent Application No. PN 1239/95 filed on Feb. 20, 1995.

The present invention relates generally to molecules such as peptides, polypeptides and proteins which interact immunologically with antibodies or T-cells in subjects having pre-clinical or clinical Insulin-Dependent Diabetes Mellitus (IDDM). These molecules are preferentially immunoreactive to T-cells in subjects having pre-clinical or clinical IDDM and are useful in the development of diagnostic, therapeutic and prophylactic agents for IDDM.

Amino acid sequences are referred to herein by sequence identity numbers (SEQ ID NOs) which are defined at the end of the specification.

Throughout this specification, unless the context requires otherwise, the word "comprise", or variations such as "comprises" or "comprising", will be understood to imply the inclusion of a stated element or integer or group of elements or integers, but not to the exclusion of any other element or integer or group of elements or integers.

Insulin-Dependent Diabetes Mellitis is a serious disease resulting from the destruction of insulin-secreting β-cells, probably mediated by T cells that recognise β-cell autoantigens. A major antigen implicated in T-cell mediated β-cell destruction characteristic of IDDM is glutamic acid decarboxylase (GAD), which occurs in two major isoforms, GAD 65 and GAD 67. These two isoforms have approximately 65% similarity at the amino acid sequence level. Subjects with IDDM or at high-risk of the disease show autoantibody and autoreactive T-cell responses to GAD insulin or both autoantigens. In NOD mice, an animal model for spontaneous IDDM, GAD is a dominant and early target antigen (Tisch et al *Nature* 366:72-75, 1993).

Identification of the immunodominant epitope(s) of pathogenic autoantigens involved in β-cell autoimmunity could lead to improved methods of diagnosis as well as therapeutic strategies to prevent IDDM.

In work leading up to the present invention, the inventors sought to identify immunodominant epitopes in GAD and proinsulin molecules in order to improve upon current diagnostic procedures and to further develop therapeutic and prophylactic compositions and treatment approaches for IDDM.

In accordance with the present invention, peptides were synthesised based on a thirteen amino acid region of high similarity between the sequences of human GAD 65 (amino acid residue numbers 506-518) and human proinsulin (amino acid residue numbers 24-36), which region of similarity also extends to human GAD 67 and mouse proinsulins and mouse GADs (FIG. 1). The immunoreactivity of these peptides is identified in accordance with the present invention on the basis of interactivity of peripheral blood cells or T-cells obtained from the peripheral blood of subjects with pre-clinical or clinical IDDM, thereby forming the basis for a new range of diagnostic, therapeutic and prophylactic procedures for IDDM.

Accordingly, one aspect of the present invention provides a recombinant or synthetic peptide or chemical equivalents thereof of the formula:

$$X_1X_2X_3$$

Wherein:
$X_1$ and $X_3$ may be the same or different and each is an amino acid sequence comprising from 0 to 40 naturally or non-naturally occurring amino acid residues; $X_2$ is any amino acid sequence of from 10 to 100 residues derived from, homologous to or contiguous within amino acids 506 to 518 inclusive or derivatives thereof of human GAD65 and/or amino acids 24 to 36 inclusive or derivatives thereof of human proinsulin; and wherein said peptide molecule is capable of reacting with T cells and modifying T-cell function when incubated with cells from subjects having pre-clinical or clinical Insulin-Dependent Diabetes Mellitus (IDDM). Preferred cells include but are not limited to peripheral blood mononuclear cells (PBMCs), anticoagulated whole blood and tissue biopsy cells.

Reference to a "peptide" includes reference to a polypeptide or protein or parts thereof.

In a preferred embodiment $X_2$ comprises not less than about 10 and not greater than about 50, amino acid residues, more preferably not less than about 10 and not greater than about 30 amino acid residues and even more preferably not less than about 10 and not greater than about 15.

In a particularly preferred embodiment $X_2$ has either of the following amino acid sequences:

```
F F Y T P K T R R E A E D    [SEQ ID NO:1]; or

F W Y I P P S L R T L E D    [SEQ ID NO:23].
```

According to this preferred embodiment, there is provided a recombinant or synthetic peptide or chemical equivalent thereof comprising the sequence:

$$X_1X_2X_3$$

wherein
$X_1$ and $X_3$ may be the same or different and each is an amino acid sequence comprising from 0 to 15 naturally or non-naturally occurring amino acid residues; $X_2$ is selected from FFYTPKTRREAED (SEQ ID NO: 1) and FWYIPPSLRTLED (SEQ ID NO: 2) or a derivative or chemical equivalent thereof and wherein said peptide is capable of reacting with T cells and modifying T-cell function when incubated with cells from subjects with pre-clinical or clinical IDDM and determining reactivity by an appropriate assay. Preferred cells include but are not limited PBMCs, anti-coagulated whole blood or tissue biopsy cells and determining reactivity by an appropriate assay.

The peptides of the present invention may be prepared by recombinant or chemically synthetic means. According to a preferred aspect of the present invention, there is provided a recombinant peptide which is preferentially immunologically reactive with T-cells from individuals with clinical or pre-clinical IDDM, which is prepared by the expression of a host cell transformed with a cassette coding for the peptide sequences of the present invention. The peptide may be fused to another peptide, polypeptide or protein. Alternatively, the peptide may be prepared by chemical synthetic techniques, such as by the Merrifield solid-phase synthesis procedure. The synthetic or recombinant peptide may or may not retain GAD activity or proinsulin activity. Furthermore, although synthetic peptides of the formula given above represent a preferred embodiment, the present invention also extends to biologically pure preparations of the naturally occurring peptides or fragments thereof. By "biologically pure" is meant a preparation comprising at least about 60%, preferably at least about 70%, more preferably at least about 80% and still more preferably at least about 90% or greater as determined by weight, activity or other suitable means.

By "pre-clinical IDDM" as used herein means those subjects who may or may not be first degree relatives of someone with IDDM who have genetic and/or immune markers of pancreatic islet (β) cell autoimmunity. By "immune markers" is meant amongst other parameters known to those in the art to include circulating antibodies and/or T-cells reactive with islet (β) cell autoantigens.

By "derivatives" as used herein is taken to include any single or multiple amino acid substitution, deletion and/or addition relative to the naturally occurring amino acid sequence in the native molecule from which the peptide is derived including any single or multiple substitution, deletion and/or addition of other molecules associated with the peptide, including carbohydrate, lipid and/or other proteinacious moieties. Such derivatives, therefore, include glycosylated or non-glycosylated forms or molecules with altered glycosylation patterns.

By the term "reacting with T cells and modifying T-cell function" as used herein is taken to include T-cell activation, T-cell inactivation and/or T-cell death.

The present invention also covers chemical analogues of the subject peptides which include, but is not limited to, modifications to side chains, incorporation of unnatural amino acids and/or their derivatives, during peptide synthesis and the use of cross-linkers and other methods which impose conformational constraints on the peptides or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbarnoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The invention also extends to use of the peptides, or derivatives thereof of the present invention in the treatment of patients. In this latter aspect, such methods of treatment include their use as an adsorbent to remove autoantibodies or autoreactive cells from a patient, their use in direct administration to a patient as a means of desensitising or inducing immunological tolerance or other mechanisms to eliminate or diminish reactivity of autoreactive T-cells or autoantibodies to IDDM autoantigens or to generate T-cell lines or clones to be used for or as therapeutic agents.

According to this aspect of the present invention, there is provided a method of treatment comprising administering to a subject an effective amount of a peptide or chemical equivalent thereof for a time and under conditions sufficient to remove or substantially reduce the presence or function in said subject of autoreactive T-cells and/or autoantibodies to IDDM autoantigens wherein the peptide comprises the formula:

$$X_1X_2X_3$$

Wherein:

$X_1$ and $X_3$ may be the same or different and each is an amino acid sequence comprising from 0 to 40 naturally or non-naturally occurring amino acid residues; $X_2$ is any amino acid sequence of from 10 to 100 residues derived from, homologous, to or contiguous within amino acids 506 to 518 inclusive or derivatives thereof of human GAD65 and/or amino acids 24 to 36 inclusive or derivatives thereof of human proinsulin; and wherein said peptide molecule is capable of reacting with T cells and modifying T-cell function when incubated with cells from subjects having clinical or pre-clinical Insulin-Dependent Diabetes Mellitus (IDDM). Preferred cells include but are not limited to peripheral blood mononuclear cells (PBMCs), anticoagulated whole blood and tissue biopsy cells.

The method of treatment contemplated herein includes, but is not limited to, the following examples. A first example of treatment is desensitisation or tolerance induction using an effective amount of synthetic peptide or derivative thereof to alter T-cell recognition of or response to GAD and/or proinsulin and/or other IDDM antigens and/or induce T-cell suppression or regulation. This may be achieved by using the known effect of certain ultraviolet wavelengths, especially UV-B, to modify antigen presentation through the skin or transmucosal or systemic administration. Effective amounts of the peptides or derivatives thereof would be applied epicutaneously to the skin of subjects exhibiting peripheral blood T-cell reactivity to GAD or proinsulin peptides or polypeptides. After exposure of skin to UV-B radiation, treatment would be repeated until such time that T-cell reactivity to GAD or proinsulin was suppressed.

A second example of treatment is to induce mucosal-mediated tolerance using an effective amount of the subject peptides or derivatives thereof to alter T-cell recognition of or response to GAD and/or pro-insulin and/or other IDDM antigens and/or induce T-cell suppression using an effective amount of peptide or derivative thereof to alter T-cell recognition of or response to GAD and/or pro-insulin and/or other IDDM antigens and/or induce T-cell suppression by the administration of the peptide or derivatives thereof by oral, aerosol or intranasal means amongst other routes of mucosal administration.

Another treatment involves application of the subject peptides to the skin together with one or more cytokines such as but not limited to TNFα or β. A further treatment involves systemic administration of soluble peptide via subcutaneous or intravenous routes to induce immunological tolerance. Yet another treatment involves T-cell immunisation whereby T-cell lines are generated to GAD or proinsulin peptide or polypeptide or fragments thereof by standard procedures, cells attenuated by fixation with agents such as glutaraldehyde or paraformaldehyde, washed under sterile conditions and re-injected into patients for a time and under conditions to cause suppression of the endogenous T-cell response to autoantigens. These approaches are applicable to the prevention of IDDM progression in asymptomatic subjects with pre-clinical IDDM or subjects with recent—onset clinical IDDM, as well as to the recurrence of IDDM in subjects who have received pancreas, islet cell or insulin-producing cell transplants. These approaches are also applicable to Stiff Man Syndrome (SMS) and other diseases where GAD and/or pro-insulin is an autoantigen.

In accordance with the present invention, the effective amount of peptide is 0.1 μg to 10 mg per dose and preferably 1.0 μg to 1 mg per dose. A dose may comprise a single administration or protocol comprising single or multiple administration hourly, daily, weekly or monthly or at other suitable times. Administration may be by any convenient means such as, but not limited to, intravenous, subcutaneous, epicutaneous, infusion, oral, topical, intranansal, aerosol suppository or intraperitoneal administration. The peptide may be administered alone or in combination with one or more other active molecules such as molecules which facilitate the activity or action of the peptide for example lipopolysaccharide (LPS), choleratoxin β-chain, Lymphocyte Functional Associated Antigen-3 (LFA-3), other adjuvants and in particular, tumour necrosis factor α (TNF-α), tumour necrosis factor β (TNF-β) or leukaemia inhibitory factor (LIF).

In yet a further embodiment, the present invention contemplates the use of the peptides described herein to measure reactivity of a subject's cells to the IDDM autoantigen. The peptides or derivatives thereof may be added in solution or bound to a solid support together with cells derived from peripheral blood or from tissue biopsies either unfractionated, fractionated or derived as continuous cell lines. Reactivity to the autoantigen may then be measured by standard proliferation assays such as incorporation of tritiated thymidine, standard cytotoxic assays such as release of marker radioactivity from target cells, measurements of expressed or secreted molecules such as surface markers, cytokines or other standard assays of cellular reactivity which are well known in the art.

According to this aspect of the present invention, there is provided a method of assaying the reactivity of a subject to IDDM autoantigen, said method comprising contacting a peptide or chemical equivalent thereof comprising the formula:

$X_1X_2X_3$

Wherein:

$X_1$ and $X_3$ may be the same or different and each is an amino acid sequence comprising from 0 to 40 naturally or non-naturally occurring amino acid residues; $X_2$ is any amino acid sequence of from 10 to 100 residues derived from, homologous to or contiguous within amino acids 506 to 518 inclusive or derivatives thereof of human GAD65 and/or amino acids 24 to 36 inclusive or derivatives thereof of human proinsulin; and wherein said peptide molecule is capable of reacting with T cells and modifying T-cell function when incubated with cells from subjects having pre-clinical or clinical Insulin-Dependent Diabetes Mellitus (IDDM) and determining reactivity by appropriate assay. In accordance with this assay, any cell type may be used but is preferably selected from PBMC's, anti-coagulated whole blood cells or tissue biopsy cells.

Preferably the present invention contemplates a method of assaying the reactivity of a subject to IDDM autoantigen said method comprising contacting a peptide or chemical equivalent thereof comprising the formula $X_1X_2X_3$ wherein:

$X_1$ and $X_3$ may be the same or different and each is an amino acid sequence comprising from 0 to 15 naturally or non-naturally occurring amino acid residues; $X_2$ is selected from FFYTPKTRREAED (SEQ ID NO: 1) and FWY-IPPSLRTLED (SEQ ID NO: 2) or a derivative or chemical equivalent thereof and wherein said peptide is capable of reacting with T cells and modifying T-cell function when incubated with cells from subjects with pre-clinical or clinical IDDM and determining reactivity by an appropriate assay. Preferably cells include but are not limited to peripheral blood mononuclear cells (PBMCs), anticoagulated whole blood and tissue biopsy cells.

In another embodiment of the present invention, there is provided a diagnostic kit for assaying T cells. Standard 96-well plates, as used in ELISA, are pre-coated with a monoclonal antibody (MAb) to a T-cell cytokine such as γ-interferon (γ-IFN) with or without antigen. Alternatively, antigen is added in soluble form together with aliquots of peripheral blood, peripheral blood mononuclear cells or T-cells. Incubation is allowed to proceed for one or more days, the supernatant (comprising medium and plasma) and the cells are washed off, wells washed again and plates developed with a labelled second MAb to the cytokine such as anti-γ-IFN conjugated with alkaline phosphatase or horseradish peroxidase. Colorimetric reaction and read-out systems can then be utilised. Alternatively, soluble cytokines (eg: γ-IFN) are measured in the supernatant by standard assays such as ELISA; further it is possible to visualise microscopically by the ELISPOT technique individual spots on bottoms of wells representing cytokine produced at the single cell level thereby enabling the frequency of peptide-epitope-reactive T-cells to be determined.

The present invention will now be further described with reference to the following non-limiting Figures and Examples.

Figure 1:
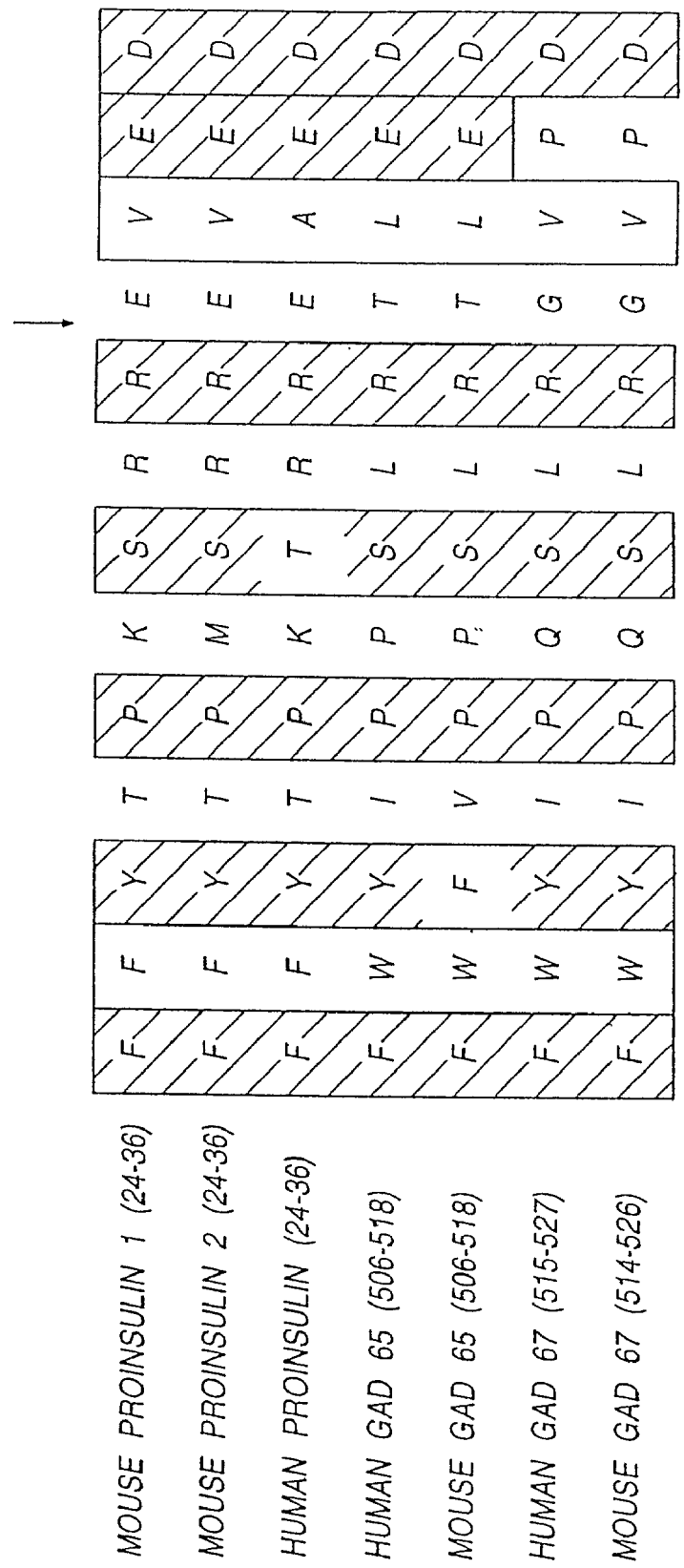
FIG. 1 shows a comparison of the regions of similarity among mouse and human proinsulins and GADs (SEQ ID NOS:1-7). Similarities are boxed; identities within boxes are shaded. The C-terminus of the mature insulin B-chain and the pro-insulin cleavage site are indicated by the vertical line and arrow respectively.

The following single and three letter abbreviations are used for amino acid residues:

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

EXAMPLE 1

Subjects

Subjects at-risk for IDDM were from the Melbourne Pre-diabetes Family Study, Victoria, Australia. Each was entered on the basis of having at least one first degree relative with IDDM and islet cell antibodies (ICA)≧20 JDF units and/or insulin autoantibodies (IAA)≧100 nU/ml. All had normal fasting blood glucose and glycated hemoglobin and had had repeat antibody and metabolic tests at six monthly intervals.

Control subjects were HLA-DR matched, asymptomatic, and without history of IDDM.

All subjects gave informed, signed consent and the study was approved by the Ethics Committees of the Royal Melbourne Hospital and the Walter and Eliza Hall Institute of Medical Research. Details of Subjects are described in Table 1.

EXAMPLE 2

HLA Typing and Assays of ICA, IAA, GAD Ab, FPIR

HLA Typing

HLA class I (A, B, C) and HLA class II (DR,DQ) typing was performed using populations of T and B lymphocytes respectively. The cells were isolated from anticoagulated blood using magnetic beads (Dynal) coated with monoclonal antibodies to CD8 (class I) or a monomorphic determinant on the class II beta chain (class II). The enriched cell populations were typed in a standard microlymphocytotoxicity assay using a battery of 240 allosera for class I and 120 allosera for class II.

Antibody Assays

ICA were assayed using indirect immunofluorescence on blood group O donor pancreas. Titres, in JDF units, were determined by doubling dilution of positive sera and comparison with standard sera run in each assay. The assay has been included in all International Diabetes Workshops and proficiency programs.

IAA were assayed by a radiobinding assay which has been internationally standardised. The upper limit for normal control sera is 40 nU insulin bound/ml serum.

GAD antibodies were assayed by immunoprecipitation of GAD enzymatic activity from piglet brain extract. The mean plus (three) 3 SD of 72 healthy subjects, 460 nU/ml, was used to define the normal range.

First phase insulin release (FPIR)

FPIR was calculated as the sum of serum insulin concentrations at 1 and 3 minutes following the completion of intravenous glucose (0.5 g/kg body weight) injected over 3 minutes.

EXAMPLE 3

T-Cell Proliferation Assay

Blood was drawn from paired IDDM at-risk and HLA-DR matched controls at the same time (within 30 minutes) and processed similarly to reduce the effects of diurnal variation and handling artifacts. Peripheral blood mononuclear cells were isolated from heparinised whole blood by Ficoll-Paque (Pharmacia Biotech) density centrifugation, washed and resuspended in RPMI 1640 medium (Biosciences Pty Ltd) containing 20 mM Hepes (CSL Ltd), $10^{-5}$ M2-mercaptoethanol (BDH), penicillin (100 U/ml), streptomycin (100 μg/ml) and 10% v/v autologous plasma. Aliquots of 200 μl($2\times10^5$ cells) were transferred into wells of a 96-well, round-bottomed plate (Falcon) and incubated in replicates of six with the following peptides as final concentrations of 10, 2, and 0.4 μg/ml: human GAD65 (506-518), human proinsulin (24-36) (synthesized using an Applied Biosystems Model 431A synthesizer (ABI, Foster City, Calif.), and an irrelevant control peptide (CRFDPQFALTNIAVRK) SEQ ID NO:8 (Macromolecular Resources, Fort Collins, Colo.). Tetanus toxoid (CSL Ltd, Melbourne, Australia) at final concentrations of 1.8, 0.18 and 0.018 LfU/ml was used as a positive control. Twelve "autologous only" wells containing cells but without antigen were included as the background control. Plates were incubated at 37° C. in a 5% v/v $CO_2$ humidified incubator for 6 days; 0.25 μCi of [$^3$H]thymidine (ICN) was added to each well for the last 6 hours. The cells were then harvested onto glass fibre filters and incorporated radioactiv ity measured by beta-particle counting (Packard Model 2000 Liquid Scintillation Counter). The level of cellular proliferation was expressed as the delta score (DS=mean counts per minute (cpm) incorporated in the presence of antigen, minus the mean cpm of the "autologous only" wells).

EXAMPLE 4

T-cell Proliferative Responses

T-cell proliferative responses to the similar 13-mer peptides from proinsulin and GAD were compared for ten pairs of HLA-DR matched at-risk and control subjects. HLA-DR matching was thought to be important not only because of the specificity of peptide binding to MHC class II alleles but also because of the known association between MHC class II and IDDM. Therefore, T-cell responses would reflect IDDM rather than MHC specificity . Responses to the highest concentration of either peptide were significantly (proinsulin, $p<0.008$; GAD, $p<0.018$-Wilcoxon one-tailed paired analysis) greater among IDDM at-risk than control subjects. The results are summarised in Table 2.

Figure 2:
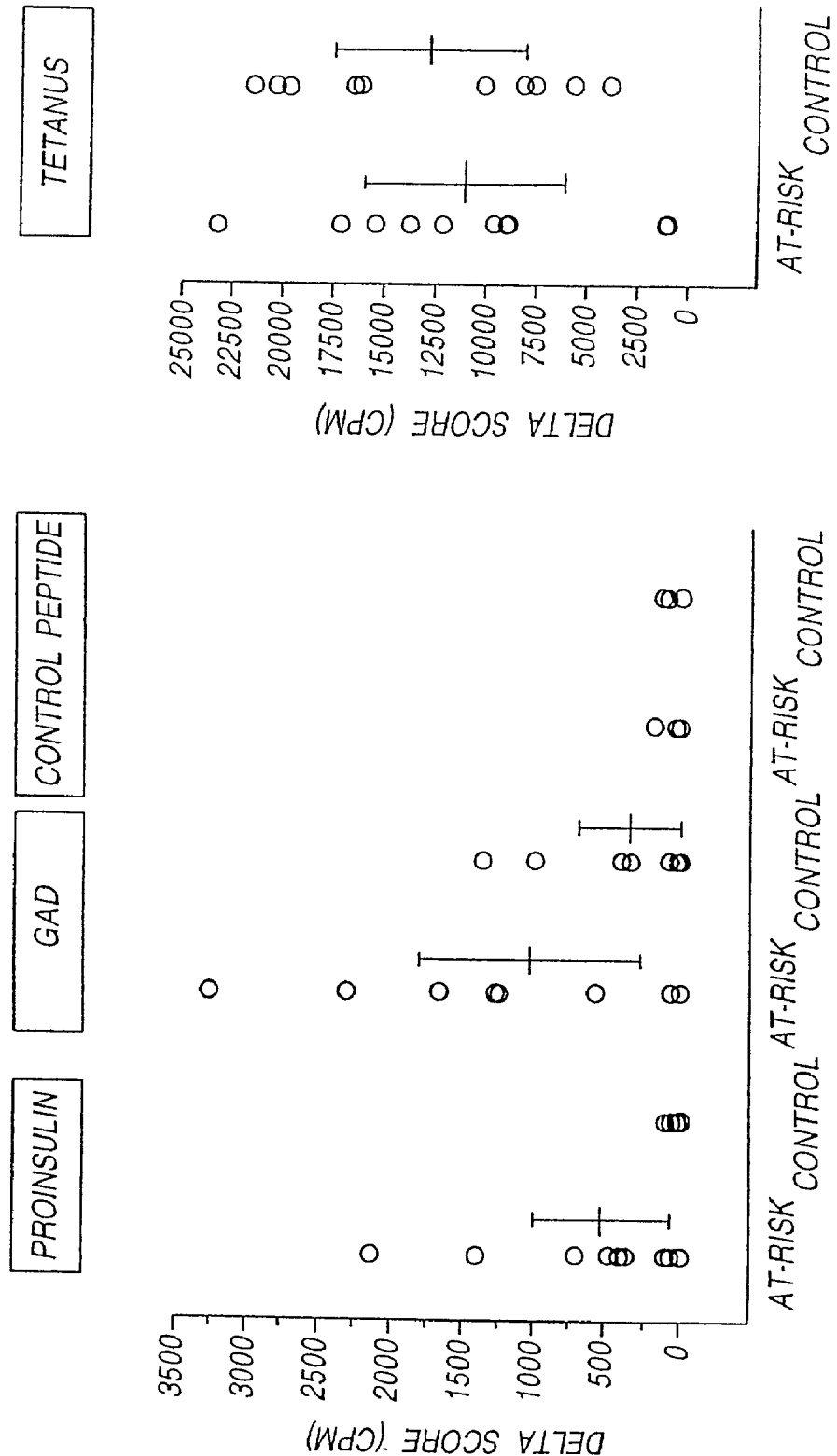
FIGS. 2A and 2B are graphical representations showing the level of cellular proliferation expressed as the delta score following the stimulation of peripheral blood mononuclear cells taken from IDDM at-risk (as described in Example 1) or control subjects with the following peptides in FIG. 2A: human GAD65 (residues 506-518); human proinsulin (residues 24-36); irrelevant control peptide; or in FIG. 2B tetanus toxoid (CSL Ltd., Melbourne, Australia).

Reactivity to the proinsulin sequence was confined almost entirely to IDDM at-risk subjects, whereas some controls also responded to the GAD peptide (Table 2, FIGS. 2A and 2B). Both groups responded similarly to tetanus, and no subject reacted to the unrelated control peptide.

For six of these pairs (#1, 2, 3, 5, 6, 7) the assay was performed on a separate occasion, but using twice as many cells ($4\times10^5$ per well). Exhaustion of the media resulted in unreliable results in three cases. In two of the other three (#5 and 6), the results were consistent with those tabulated here, while in the third (#3) the at-risk subject displayed greater reactivity to both antigens at the higher cell number.

EXAMPLE 5

T-Cell Cytokine Secretion Assays

In a second cohort of 18 paired IDDM at-risk and HLA-DR-matched controls, PBMCs indicated as per Example 3 were incubated with human proinsulin 24-36 and human insulin B chain 1-15 each at 0.5, 5 and 50 µg/ml under the conditions as per Example 3. In addition to harvesting cells for the measurement of proliferation by [$^3$H] thymidine uptake after 6 days, as per Example 3, incubation media above the cells was sampled after 2 days for the measurement of IFN-$\gamma$ and interleukin-(IL-) 10 by standard ELISA methods.

EXAMPLE 6

T-Cell Responses

Figure 3:
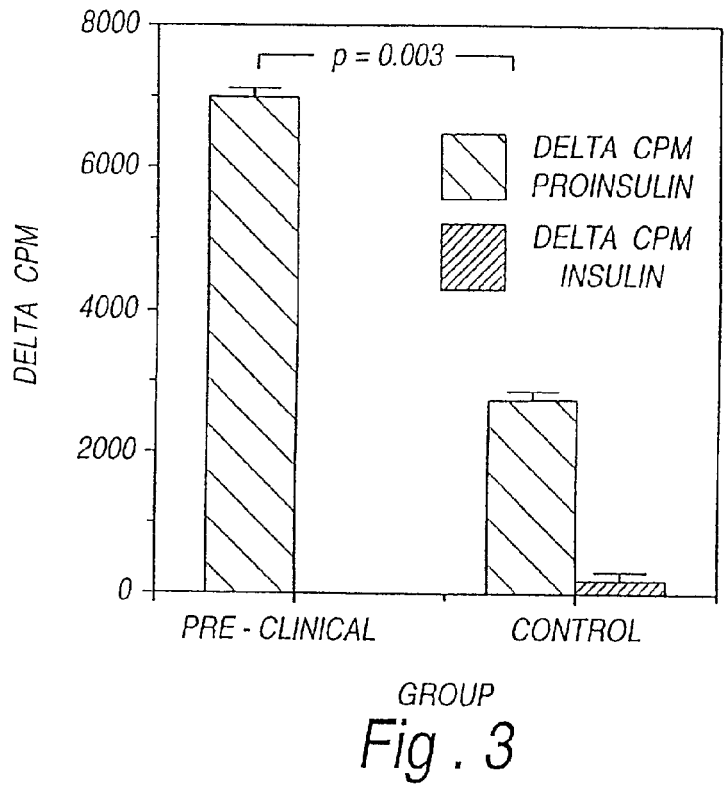
FIG. 3 is a graphical representation showing proliferation (mean+sem) of pbmc to proinsulin (aa 24-36) and insulin (aa 1-15) in pre-clinical and control subjects.
Figure 4:
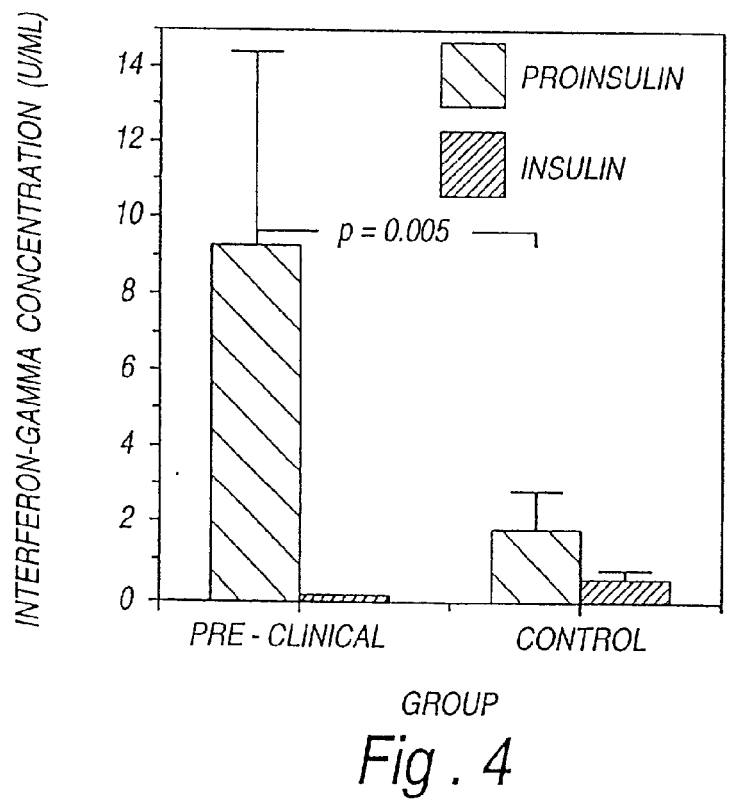
FIG. 4 is a graphical representation showing IFN-gamma response (mean+sem) to proinsulin (aa 24-36) and insulin beta chain (aa 1-15) in pre-clinical and control subjects.
Figure 5:
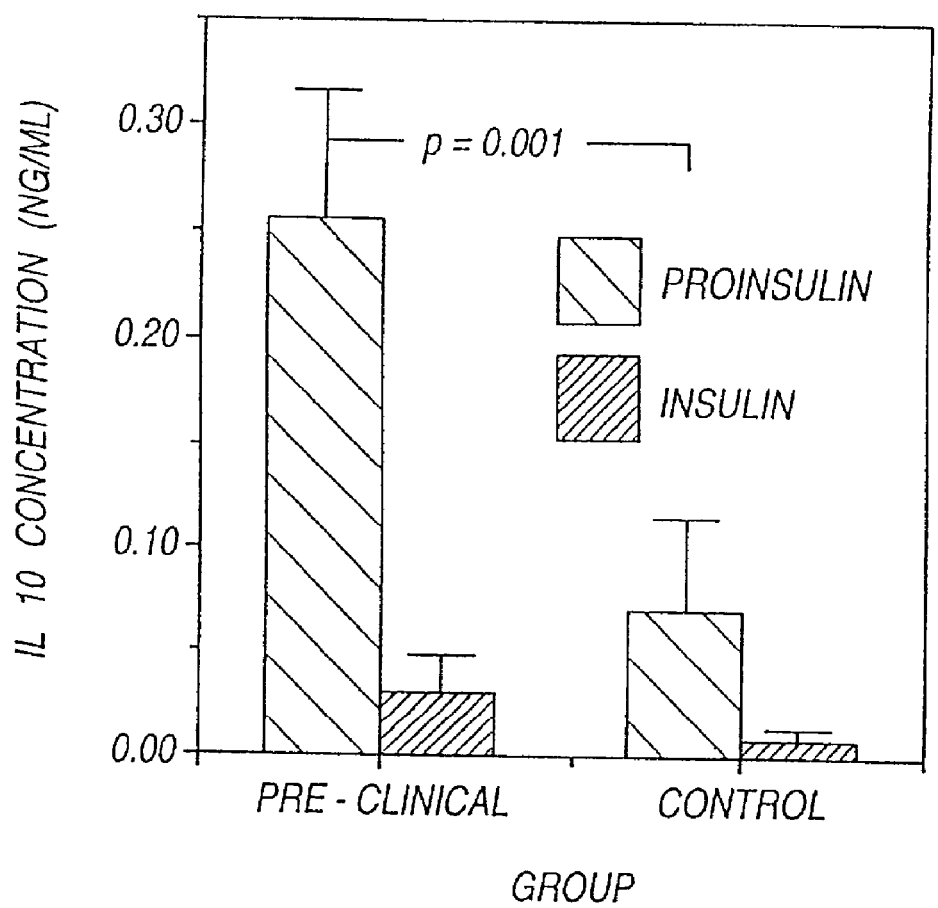
FIG. 5 is a graphical representation showing IL10 response (mean+sem) to proinsulin (aa 24-36) and insulin beta-chain (aa 1-15) in pre-clinical and control subjects.

T-cell proliferative and IFN-$\gamma$ and IL-10 secretory responses to human proinsulin 24-36 and human insulin B 1-15 were compared for 18 pairs of HLA-DR matched IDDM at-risk and control subjects. As per Example 4, there was a significantly greater ($p=0.003$) proliferative response of IDDM at-risk subjects to the proinsulin peptide (FIG. 3). In addition, both IFN-$\gamma$ and IL-10 secretion in response to the proinsulin peptide were significantly increased ($p=0.005$ and $p=0.001$, respectively) compared to matched control subjects (FIGS. 4, 5).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| Subject # | Age | Years Follow-up | HLA A | B | DR | DQ | ICA * | IAA † |
|---|---|---|---|---|---|---|---|---|
| 1 | 14 | 1.6 | 1 | 8 | 3 | 2 | 160,69,56 | 4,30,−20 |
| 2 | 23 | 4.8 | 2 | 44,55 | 3,4 | 5,8 | 55,37,14,6,5,5 | −25,9,41,−2,0,44 |
| 3 | 22 | 6.8 | 2,28 | 7,8 | 3,4 | 2,8 | 37,37,37,37,52,30,58,46,26 | 8,9,2,31,7,9,−41,−1,64 |
| 4 | 13 | 1.3 | 1,11 | 8,27 | 3,4 | 2,8 | 160,190 | 84,280 |
| 5 | 25 | 5.5 | 2 | 44,62 | 4,11 | 7,8 | 0,19,18,16,22,0,0 | 45,31,42,60,29,130,30 |
| 6 | 20 | 5.5 | 1,2 | 8,62 | 3,4 | 2,8 | 19.19.104.86.8 | 480,560,400,130,300 |
| 7 | 18 | 1.7 | 1,3 | 8,18 | 3 | 2 | 69,69 | 13,20 |
| 8 | 9 | 3.2 | 1,2 | 8,44 | 3,4 | 2,8 | 160,160,160,160 | −2,−26,36,59 |
| 9 | 10 | 2.8 | 1,2 | 8,27 | 3,4 | 2,8 | 160,160,120,24 | 2,29,14,120 |
| 10 | 14 | 4.8 | 1,32 | 8,14 | 4,7 | 2,8 | 14,13,51,18 | 240,490,470,1000 |

| Subject # | Age | Years Follow-up | GAD Ab £ | FPIR ¶ |
|---|---|---|---|---|
| 1 | 14 | 1.6 |  | 118,155 |
| 2 | 23 | 4.8 | 278,602 | 124,113,57 |
| 3 | 22 | 6.8 | 1637,2259,634,1535 | 183,155,140,161,56 |
| 4 | 13 | 1.3 |  | 79,91 |
| 5 | 25 | 5.5 | 736,936,1336,790,810 | 137,143,68,15 |
| 6 | 20 | 5.5 | 937,2258,2389 | 105,238,165,128 |
| 7 | 18 | 1.7 |  | 44,47 |
| 8 | 9 | 3.2 | 2300,1830 | 118,129,87 |
| 9 | 10 | 2.8 | 1525,1388 | 26,56,29 |
| 10 | 14 | 4.8 | 432 | 318,181,165 |

* ICA = islet cell antibody titres (JDF units)
† IAA = insulin autoantibody titres (nU insulin bound/ml serum)
£ GADAb = glutamic acid decarboxylase autoantibody titres (nU/ml)
¶ FPIR = first phase insulin release (sum of serum insulin concentrations at 1 and 3 minutes following completion of glucose injection)

TABLE 2

| | Delta Scores* | | | | | | | |
|---|---|---|---|---|---|---|---|---|
| | Autologous | | Proinsulin 10 μg/ml | | Proinsulin 2 μg/ml | | Proinsulin 0.4 μg/ml | |
| Pair # | At Risk | Control | At Risk | Control | At Risk | Control | At Risk | Control |
| 1 | 881 | 2979 | 1391 | 0 | 459 | 0 | 1040 | 0 |
| 2 | 236 | 389 | 351 | 0 | 0 | 0 | 33 | 0 |
| 3 | 6515 | 217 | 0 | −64 | 355 | 43 | 0 | 0 |
| 4 | 595 | 1347 | 104 | 0 | 0 | 0 | 288 | 0 |
| 5 | 1745 | 1269 | 694 | 0 | 0 | 0 | 0 | 0 |
| 6 | 1007 | 265 | 397 | 98 | 65 | 380 | 0 | 0 |
| 7 | 1392 | 454 | 467 | 93 | 0 | 0 | 0 | 0 |
| 8 | 9993 | 308 | 2128 | 0 | 1367 | 0 | 0 | 0 |
| 9 | 598 | 135 | 0 | 0 | 265 | 13 | 0 | 0 |
| 10 | 597 | 870 | 56 | 21 | 0 | 22 | 0 | 0 |
| Mean | 2355.8 | 823.4 | 558.7 | 27.6 | 251.1 | 45.8 | 136.0 | 0 |
| Std. Error | 1025.7 | 276.2 | 219.5 | 13.0 | 135.3 | 37.4 | 104.4 | 0 |
| Wilcoxon P-Value (One-Tailed) | | | 0.008 | | 0.125 | | 0.054 | |

| | Delta Scores* | | | | | |
|---|---|---|---|---|---|---|
| | GAD 10 μg/ml | | GAD 2 μg/ml | | GAD 0.4 μg/ml | |
| Pair # | At Risk | Control | At Risk | Control | At Risk | Control |
| 1 | 579 | 0 | 516 | 0 | 768 | 0 |
| 2 | 3263 | 0 | 190 | 0 | 199 | 0 |
| 3 | 0 | 77 | 0 | 5 | 0 | 25 |
| 4 | 0 | 0 | 10 | 0 | 0 | 0 |
| 5 | 1275 | 20 | 394 | 120 | 53 | 30 |
| 6 | 1679 | 992 | 220 | 216 | 77 | 195 |
| 7 | 2313 | 1365 | 0 | 0 | 0 | 70 |
| 8 | 0 | 0 | 0 | 0 | 0 | 0 |
| 9 | 1251 | 337 | 0 | 0 | 255 | 21 |
| 10 | 65 | 391 | 0 | 1441 | 0 | 0 |
| Mean | 1042.4 | 318.1 | 133.0 | 178.2 | 135.3 | 34.1 |
| Std. Error | 357.1 | 153.0 | 60.5 | 142.2 | 76.0 | 19.2 |
| Wilcoxon P-Value (One-Tailed) | 0.018 | | 0.199 | | 0.199 | |

*Delta Score = mean of six replicate wells minus mean of twelve autologous wells (if less than 0, shown as 0)

---

The invention claimed is:

1. A method for determining the reactivity of a subject to IDDM autoantigen, comprising,
   1) contacting T-cells derived from the subject with a peptide consisting of FFYTPKTRREAED (SEQ ID NO: 1), and,
   2) measuring the reactivity of said T-cells to said peptide by an appropriate assay thereby determining the reactivity of said subject to IDDM autoantigen.

2. A method according to claim 1 wherein the T-cells are isolated from samples selected from the group consisting of PBMCs, anti-coagulated whole blood and tissue biopsy cells.

3. A method according to claim 1 or 2 wherein an appropriate assay includes a proliferation assay, cytotoxic assays, cellular reactivity or a combination thereof.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 13 amino acids
      (B) TYPE: amino acid
      (C) STRANDEDNESS: not relevant
      (D) TOPOLOGY: linear (ii) MOLECULE TYPE: protein (xi) SEQUENCE DESCRIPTION: SEQ ID NO: 1:

Phe Phe Tyr Thr Pro Lys Thr Arg Arg Glu Ala Glu Asp
1               5                   10

(2) INFORMATION FOR SEQ ID NO: 2:

(i) SEQUENCE CHARACTERISTICS:
      (A) LENGTH: 13 amino acids
      (B) TYPE: amino acid
      (C) STRANDEDNESS: not relevant (D) TOPOLOGY: linear (ii) MOLECULE TYPE: protein (xi) SEQUENCE DESCRIPTION: SEQ ID NO: 2:

Phe Trp Tyr Ile Pro Pro Ser Leu Arg Thr Leu Glu Asp
1               5                  10

(2) INFORMATION FOR SEQ ID NO: 3:

(i) SEQUENCE CHARACTERISTICS:
        (A) LENGTH: 13 amino acids
        (B) TYPE: amino acid
        (C) STRANDEDNESS: not relevant
        (D) TOPOLOGY: linear (ii) MOLECULE TYPE: protein (xi) SEQUENCE DESCRIPTION: SEQ ID NO: 3:

Phe Phe Tyr Thr Pro Lys Ser Arg Arg Glu Val Glu Asp
1               5                  10

(2) INFORMATION FOR SEQ ID NO: 4:

(i) SEQUENCE CHARACTERISTICS:
        (A) LENGTH: 13 amino acids
        (B) TYPE: amino acid
        (C) STRANDEDNESS: not relevant
        (D) TOPOLOGY: linear (ii) MOLECULE TYPE: protein (xi) SEQUENCE DESCRIPTION: SEQ ID NO: 4:

Phe Phe Tyr Thr Pro Met Ser Arg Arg Glu Val Glu Asp
1               5                  10

(2) INFORMATION FOR SEQ ID NO: 5:

(i) SEQUENCE CHARACTERISTICS:
        (A) LENGTH: 13 amino acids
        (B) TYPE: amino acid
        (C) STRANDEDNESS: not relevant
        (D) TOPOLOGY: linear (ii) MOLECULE TYPE: protein (xi) SEQUENCE DESCRIPTION: SEQ ID NO: 5:

Phe Trp Phe Val Pro Pro Ser Leu Arg Thr Leu Glu Asp
1               5                  10

(2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS: not relevant
        (D) TOPOLOGY: linear (ii) MOLECULE TYPE: protein (xi) SEQUENCE DESCRIPTION: SEQ ID NO: 6:

Phe Trp Tyr Ile Pro Gln Ser Leu Arg Gly Val Pro Asp
1               5                  10

(2) INFORMATION FOR SEQ ID NO: 7:

(i) SEQUENCE CHARACTERISTICS:
        (A) LENGTH: 13 amino acids
        (B) TYPE: amino acid -continued

```
            (C) STRANDEDNESS: not relevant
            (D) TOPOLOGY: linear (ii) MOLECULE TYPE: protein (xi) SEQUENCE DESCRIPTION: SEQ ID NO: 7:

Phe Trp Tyr Ile Pro Gln Ser Leu Arg Gly Val Pro Asp
1               5                   10

(2) INFORMATION FOR SEQ ID NO: 8:

(i) SEQUENCE CHARACTERISTICS:
            (A) LENGTH: 16 amino acids
            (B) TYPE: amino acid
            (C) STRANDEDNESS: not relevant
            (D) TOPOLOGY: linear (ii) MOLECULE TYPE: protein (xi) SEQUENCE DESCRIPTION: SEQ ID NO: 8:

Cys Arg Phe Asp Pro Gln Phe Ala Leu Thr Asn Ile Ala Val Arg Lys
1               5                   10                  15
```